United States Patent
Mr et al.

(10) Patent No.: US 11,779,904 B2
(45) Date of Patent: Oct. 10, 2023

(54) AUTOMATIC RECHARGER BRINE PREPARATION FROM A CANISTER

(71) Applicant: Mozarc Medical US LLC, Minneapolis, MN (US)

(72) Inventors: Kirankumar Mr, Bangalore (IN); Muhammed Mashal P K, Bangalore (IN)

(73) Assignee: Mozarc Medical US LLC, Minneapolis, MN (US)

( * ) Notice: Subject to any disclaimer, the term of this patent is extended or adjusted under 35 U.S.C. 154(b) by 223 days.

(21) Appl. No.: 17/152,495

(22) Filed: Jan. 19, 2021

(65) Prior Publication Data

US 2022/0226801 A1  Jul. 21, 2022

(51) Int. Cl.
*B01J 20/34* (2006.01)
*A61M 1/16* (2006.01)
*B01J 20/02* (2006.01)

(52) U.S. Cl.
CPC ........ *B01J 20/3475* (2013.01); *A61M 1/1696* (2013.01); *B01J 20/0292* (2013.01); *B01J 2220/62* (2013.01)

(58) Field of Classification Search
CPC .... B01J 20/34; B01J 20/2475; B01J 20/0292; B01J 2220/62; A61M 1/1696
USPC .......................................................... 502/25
See application file for complete search history.

(56) References Cited

U.S. PATENT DOCUMENTS

| 2020/0061269 A1* | 2/2020 | Dutta | B01J 20/3475 |
| 2022/0226552 A1* | 7/2022 | Mr | A61M 1/1696 |
| 2022/0226801 A1* | 7/2022 | Mr | B01J 20/3475 |

\* cited by examiner

*Primary Examiner* — Edward M Johnson
(74) *Attorney, Agent, or Firm* — Hahn & Associates

(57) ABSTRACT

Systems and methods for generating a brine solution using a canister for recharging zirconium phosphate in a reusable sorbent module are provided. The canister can include salt and have an inlet and an outlet. The inlet can extend upwardly into an interior of the canister above solid sodium chloride and sodium acetate. Water can be added to dissolve the salts in the canister and the resulting solution can be collected as a brine solution for use in recharging the zirconium phosphate.

20 Claims, 9 Drawing Sheets

AUTOMATIC RECHARGER BRINE PREPARATION FROM A CANISTER

FIELD

The disclosure relates to systems and methods for generating a brine solution using a canister for recharging zirconium phosphate in a reusable sorbent module. The canister can contain salt and include an inlet and an outlet. The inlet can extend upwardly into an interior of the canister above solid sodium chloride and sodium acetate. Water can be added to dissolve the salts in the canister and the resulting solution can be collected as a brine solution for use in recharging the zirconium phosphate.

BACKGROUND

Sorbent based dialysis systems can use zirconium phosphate as a sorbent material to remove potassium, calcium, and magnesium ions from spent dialysate. The zirconium phosphate is generally provided in a sorbent cartridge with other sorbent materials. After use, the spent zirconium phosphate is disposed or removed from the sorbent cartridge for further processing. However, removing spent zirconium phosphate from a sorbent cartridge, separating the zirconium phosphate from other sorbent materials, and processing the spent zirconium phosphate can require significant time and expense. Further, large quantities of solutions for processing the spent zirconium phosphate can be required along with any necessary infrastructure, storage, and transportation. Expensive manufacturing lines and plants may also be required to generate premade solutions for use in processing the zirconium phosphate.

Hence, there is a need for systems and methods that can recharge zirconium phosphate within a reusable sorbent module. There is further a need for systems and methods for generating the recharge solutions necessary for recharging the zirconium phosphate, and in particular, brine solutions. There is a need for systems and methods that can generate the brine solution on-line and quickly, reducing the manufacturing burden and reducing the storage needs and time required for preparation and recharging.

SUMMARY OF THE INVENTION

The problem to be solved by the present invention is online preparation of a brine solution for use in recharging sorbent materials. The solution is to include sodium chloride and sodium acetate in a salt canister. The sodium chloride and sodium acetate can be dissolved when needed to generate the brine solution.

The first aspect of the invention relates to a system. In any embodiment, the system can include a sorbent recharger; the sorbent recharger having: i) a receiving compartment for a zirconium phosphate sorbent module; ii) at least a first fluid line fluidly connectable to an inlet of the zirconium phosphate sorbent module in the receiving compartment; iii) at least a second fluid line fluidly connectable to an outlet of the zirconium phosphate sorbent module; and iv) at least one pump; the system further including a brine container fluidly connectable to the first fluid line; a salt canister; the salt canister having an inlet fluidly connectable to a water source and an acetic acid source; and an outlet fluidly connectable to the brine container; the salt canister containing sodium chloride and sodium acetate; and a control system; the control system programmed to: i) pump a preset volume of fluid from the water source into the salt canister; ii) recirculate fluid in a first flow path from the outlet of the salt canister to the brine container and then to the inlet of the salt canister; and to iii) pump a preset volume of acetic acid into the first flow path.

In any embodiment, the control system can be further programmed to pump fluid from the brine container through the zirconium phosphate sorbent module.

In any embodiment, the control system can be programmed to recirculate fluid in a first flow path until a homogeneous solution is generated in the first flow path.

In any embodiment, the control system can be programmed to recirculate fluid in a first flow path for a preset period of time.

In any embodiment, the salt canister can include a filter pad between the sodium chloride and sodium acetate and the outlet.

In any embodiment, the salt canister can include a cap on a bottom of the salt canister; wherein the inlet and outlet enter the salt canister through the cap.

In any embodiment, the salt canister can include a filter pad in the cap; the filter pad between the sodium chloride and sodium acetate and the outlet.

In any embodiment, the inlet of the salt canister can extend upwardly into the salt canister.

In any embodiment, the inlet of the salt canister can extend upwardly above the sodium chloride and sodium acetate in the salt canister.

In any embodiment, the salt sodium chloride and sodium acetate can be initially solid.

In any embodiment, the salt canister can be initially filled about ¾ with sodium chloride and sodium acetate.

In any embodiment, the salt canister can include an air vent at a top of the salt canister.

The features disclosed as being part of the first aspect of the invention can be in the first aspect of the invention, either alone or in combination, or follow any arrangement or permutation of any one or more of the described elements. Similarly, any features disclosed as being part of the first aspect of the invention can be in a second, third, fourth, or fifth aspects of the invention described below, either alone or in combination, or follow any arrangement or permutation of any one or more of the described elements.

The second aspect of the invention relates to a method for generating a brine solution for recharging zirconium phosphate. In any embodiment, the method can include the steps of: pumping water from a water source to a salt canister through an inlet of the salt canister; the salt canister containing sodium chloride and sodium acetate; recirculating fluid from an outlet of the salt canister, to a brine container, and back to the inlet of the salt canister in a first flow path; pumping acetic acid into the first flow path; and collecting fluid from the first flow path into the brine container to generate the brine solution.

In any embodiment, the brine container can be fluidly connected to a sorbent recharger; and the method can include the step of pumping the brine solution through a zirconium phosphate sorbent module in the sorbent recharger.

In any embodiment, the fluid can be recirculated in the first flow path until a homogenous solution is generated.

In any embodiment, the fluid can be recirculated in the first flow path for a preset period of time.

In any embodiment, the salt canister can have a filter pad between the sodium chloride and sodium acetate and the outlet.

In any embodiment, the salt canister can include a cap on a bottom of the salt canister; wherein the inlet and outlet enter the salt canister through the cap.

In any embodiment, the salt canister can include a filter pad in the cap; the filter pad between the sodium chloride and sodium acetate and the outlet.

In any embodiment, the inlet of the salt canister can extend upwardly into the salt canister.

In any embodiment, the inlet of the salt canister can extend above the sodium chloride and sodium acetate the salt canister.

In any embodiment, the salt sodium chloride and sodium acetate can be initially solid.

The features disclosed as being part of the second aspect of the invention can be in the second aspect of the invention, either alone or in combination, or follow any arrangement or permutation of any one or more of the described elements. Similarly, any features disclosed as being part of the second aspect of the invention can be in the first, third, fourth, or fifth aspects of the invention, either alone or in combination, or follow any arrangement or permutation of any one or more of the described elements.

The third aspect of the invention is drawn to a salt canister for use in recharging zirconium phosphate. In any embodiment, the salt canister can include an inlet fluidly connectable to a water source; an outlet fluidly connectable to a brine container; and a cap on a bottom of the salt canister; wherein the inlet and outlet enter the salt canister through the cap; the salt canister containing sodium chloride and sodium acetate.

In any embodiment, the salt canister can include an air vent on a top of the salt canister.

In any embodiment, the inlet of the salt canister can extend upwardly into the salt canister.

In any embodiment, the inlet of the salt canister can extend upwardly above the sodium chloride and sodium acetate in the salt canister.

The features disclosed as being part of the third aspect of the invention can be in the third aspect of the invention, either alone or in combination, or follow any arrangement or permutation of any one or more of the described elements. Similarly, any features disclosed as being part of the third aspect of the invention can be in the first, second, fourth, or fifth aspects of the invention, either alone or in combination, or follow any arrangement or permutation of any one or more of the described elements.

The fourth aspect of the invention is drawn to a sorbent recharger. In any embodiment, the sorbent recharger can include at least one inlet fluidly connectable to a water source; at least one inlet fluidly connectable to a brine container; and at least one outlet fluidly connectable to the salt canister of the third aspect of the invention.

In any embodiment, the sorbet recharger can include a control system programmed to: i) pump a preset volume of fluid from the water source into the salt canister; ii) recirculate fluid in a first flow path from the outlet of the salt canister to the brine container and then to the inlet of the salt canister; and to iii) pump a preset volume of acetic acid into the first flow path.

In any embodiment, the control system can be programmed to recirculate fluid in the first flow path until a homogeneous solution is generated in the first flow path.

In any embodiment, the control system can be programmed to recirculate fluid in a first flow path for a preset period of time.

The features disclosed as being part of the fourth aspect of the invention can be in the fourth aspect of the invention, either alone or in combination, or follow any arrangement or permutation of any one or more of the described elements. Similarly, any features disclosed as being part of the fourth aspect of the invention can be in the first, second, third, or fifth aspects of the invention, either alone or in combination, or follow any arrangement or permutation of any one or more of the described elements.

The fifth aspect of the invention is drawn to a brine container. In any embodiment, the brine container can include an inlet fluidly connectable to the salt canister of the third aspect of the invention; and an outlet fluidly connectable to a sorbent recharger.

The features disclosed as being part of the fifth aspect of the invention can be in the fifth aspect of the invention, either alone or in combination, or follow any arrangement or permutation of any one or more of the described elements. Similarly, any features disclosed as being part of the fifth aspect of the invention can be in the first, second, third, or fourth aspects of the invention, either alone or in combination, or follow any arrangement or permutation of any one or more of the described elements.

DETAILED DESCRIPTION

Figure 1A:
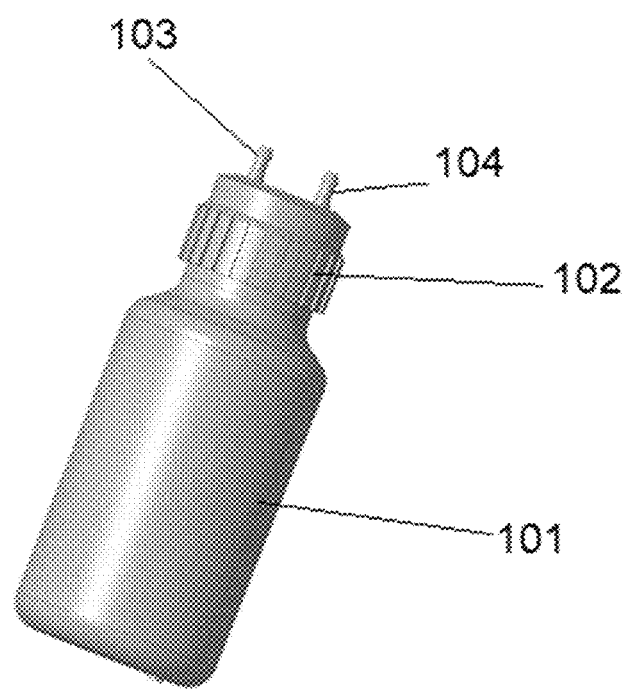
FIGS. 1A-E illustrate a salt canister for preparation of a brine solution.

Unless defined otherwise, all technical and scientific terms used have the same meaning as commonly understood by one of ordinary skill in the art.

The articles "a" and "an" are used to refer to one to over one (i.e., to at least one) of the grammatical object of the article. For example, "an element" means one element or over one element.

An "acetic acid source" is a solid, fluid, or concentrate source from which acetic acid or an acetic acid solution can be obtained.

An "air vent" is an opening through which gas can pass in a component, allowing gas to flow into or out of the component.

The term "bottom" refers to a portion of a component intended to be at a lower elevation than a "top" during normal use of the component.

A "brine container" is a container for containing a brine solution. The container can be any suitable shape, size, or form capable of containing one or more materials, such as a brine.

A "brine solution" is a solution containing sodium chloride, an acid, and the sodium salt of the acid.

A "cap" is a removable component that, when attached, covers an opening in a container or canister.

A "canister" can be a container of any shape, size, or form capable of containing one or more materials. In one non-limiting embodiment, the canister can be generally round or cylindrical in form. The canister can have one or more tapered ends. However, it will be understood that the canister can be any casing having a rectangular, elliptical, triangular, or any other form. The canister should be interpreted in the broadest sense.

To "collect" a fluid refers to flowing a volume of the fluid into a container.

The term "comprising" includes, but is not limited to, whatever follows the word "comprising." Use of the term indicates the listed elements are required or mandatory but that other elements are optional and may be present.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts, or features that do not affect the basic operation of the apparatus, structure or method described.

A "container" is a vessel or receptable of any shape, size, or form capable of containing one or more materials. The container should be interpreted in the broadest sense.

The term "containing" refers to a substance that is within a component or container.

A "control system" can be a combination of components that act together to maintain a system to a desired set of performance specifications. The control system can use processors, memory and computer components configured to interoperate to maintain the desired performance specifications. The control system can also include fluid or gas control components, and solute control components as known within the art to maintain performance specifications.

To term "extends upwardly" refers to a part of a component that is at a higher elevation vertically than the rest of the component when positioned for normal use.

A "filter pad" is a porous pad through which water or aqueous solutions can pass, but that prevents solid materials from passing.

A "flow path" is a pathway through which a fluid, gas, or combinations or mixtures thereof can travel.

A "fluid" is a liquid substance optionally having a combination of gas and liquid phases in the fluid. Notably, a liquid, as used herein, can therefore also have a mixture of gas and liquid phases of matter.

A "fluid line" can refer to a tubing or conduit through which a fluid or fluid containing gas can pass. The fluid line can also contain air during different modes of operation such as cleaning or purging of a line.

The term "fluidly connectable" refers to the ability of providing for the passage of fluid, gas, or combination thereof, from one point to another point. The ability of providing such passage can be any connection, fastening, or forming between two points to permit the flow of fluid, gas, or combinations thereof. The two points can be within or between any one or more of compartments of any type, modules, systems, components, and rechargers.

The term "fluidly connected" refers to a particular state such that the passage of fluid, gas, or combination thereof, is provided from one point to another point. The connection state can also include an unconnected state, such that the two points are disconnected from each other to discontinue flow. It will be further understood that the two "fluidly connectable" points, as defined above, can form a "fluidly connected" state. The two points can be within or between any one or more of compartments, modules, systems, components, and rechargers, all of any type.

The terms "generate," "generating," "is generated," and the like refer to forming a solution or substance from constituent parts.

The term "homogeneous solution" refers to an aqueous solution wherein the concentration of solutes is substantially identical at all parts of the solution.

The term "initially" refers to a state of a component or system prior to a process.

The term "inlet" can refer to a portion of container, flow path, or component through which fluid, gas, or a combination thereof can be drawn into the container, flow path, or component.

The term "interior" refers to an area inside of a given component or system.

The term "outlet" can refer to a portion of container, flow path, or component through which fluid, gas, or a combination thereof can be drawn out of the container, flow path, or component.

A "preset period of time" is a length of time that is set prior to a process or step.

The term "preset volume" refers to an amount of fluid determined prior to a process.

The term "programmed," when referring to a processor, can mean a series of instructions that cause a processor to perform certain steps.

The term "pump" refers to any device that causes the movement of fluids or gases by applying suction or pressure.

A "receiving compartment" can be a compartment, section, or chamber of any device or components. In one non-limiting example, the receiving compartment can be within a sorbent recharger into which a sorbent module can be positioned to be recharged.

"Recharging" refers to treating a sorbent material to restore the functional capacity of the sorbent material to put the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged."

To "recirculate" refers to moving fluid in a flow loop from a first point through the flow loop and back to the first point.

A "salt canister" can be a container or canister as defined herein, that is capable of hold or containing salts. The salts can be used to generate a brine solution. The salt canister can include an inlet for receiving water and an outlet for the formed solution to exit.

The term "sodium acetate" refers to $CH_3CO_2Na$ either solid or in an aqueous solution.

The term "sodium chloride" refers to NaCl either solid or in an aqueous solution.

The term "solid" refers to a material in the solid phase of matter, and can include crystalline, powdered, or any other form of solid material.

A "sorbent module" means a discreet component of a sorbent cartridge. Multiple sorbent cartridge modules can be fitted together to form a sorbent cartridge of two, three, or more sorbent cartridge modules. The "sorbent cartridge module" or "sorbent module" can contain any selected materials for use in sorbent dialysis and may or may not contain a "sorbent material" or adsorbent, but less than the full complement of sorbent materials needed. In other words, the "sorbent cartridge module" or "sorbent module"

generally refers to the use of the "sorbent cartridge module" or "sorbent module" in sorbent-based dialysis, e.g., REDY (REcirculating DYalysis), and not that a "sorbent material" that is necessarily contained in the "sorbent cartridge module" or "sorbent module."

A "sorbent recharger" or "recharger" is an apparatus designed to recharge at least one sorbent material.

The term "water source" refers to any source from which potable or non-potable water can be obtained.

"Zirconium phosphate" is a sorbent material that removes cations from a fluid, exchanging the removed cations for different cations.

A "zirconium phosphate sorbent module" is a sorbent module that contains zirconium phosphate.

Brine Preparation from a Salt Canister

Figure 1B:
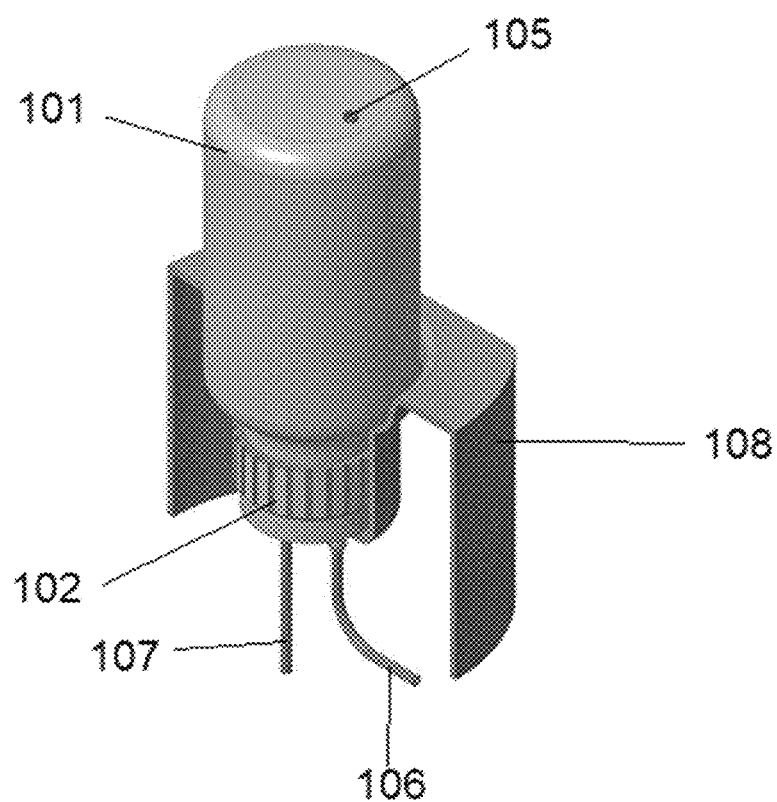
Figure 1C:
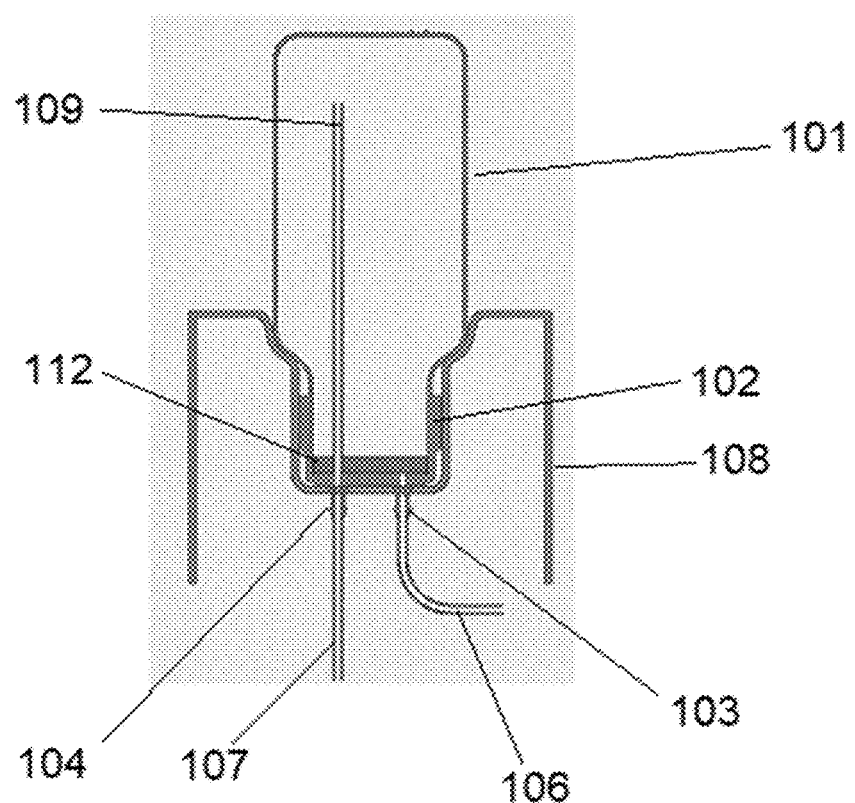
Figure 1D:
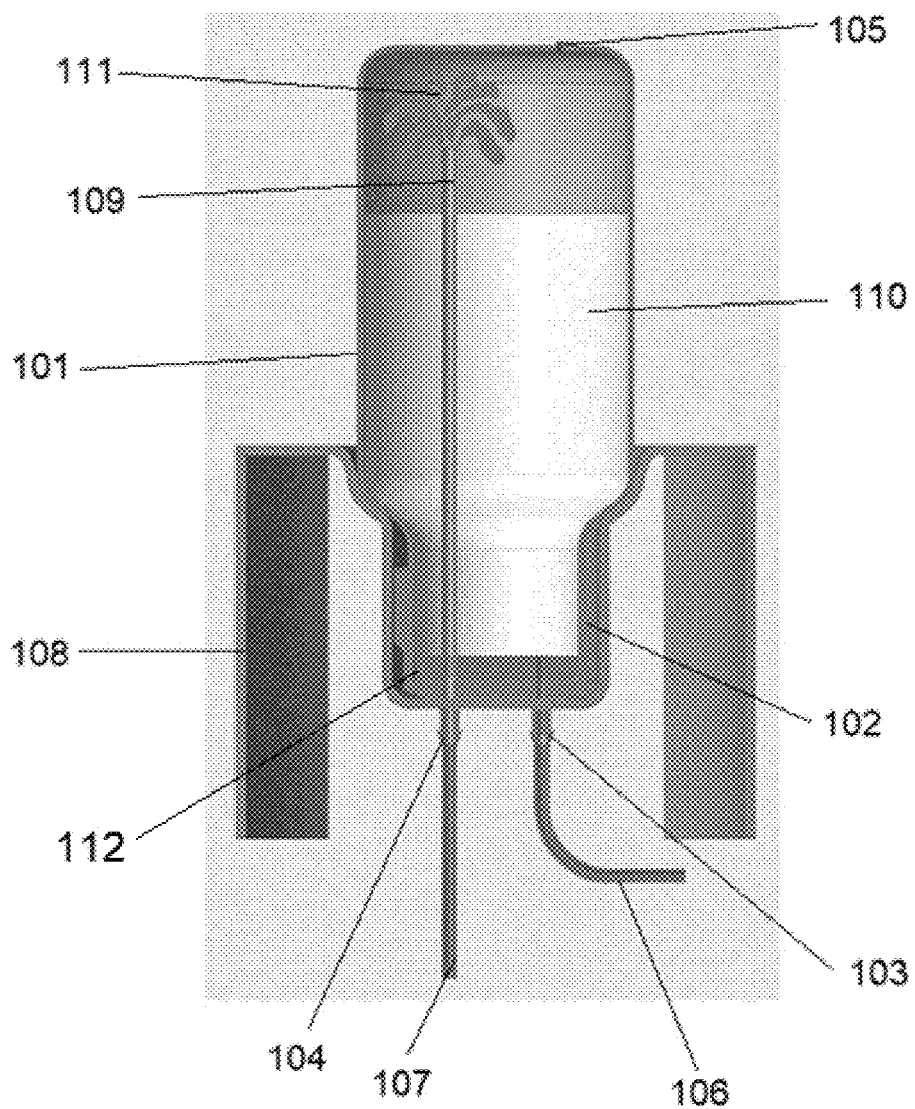
Figure 1E:
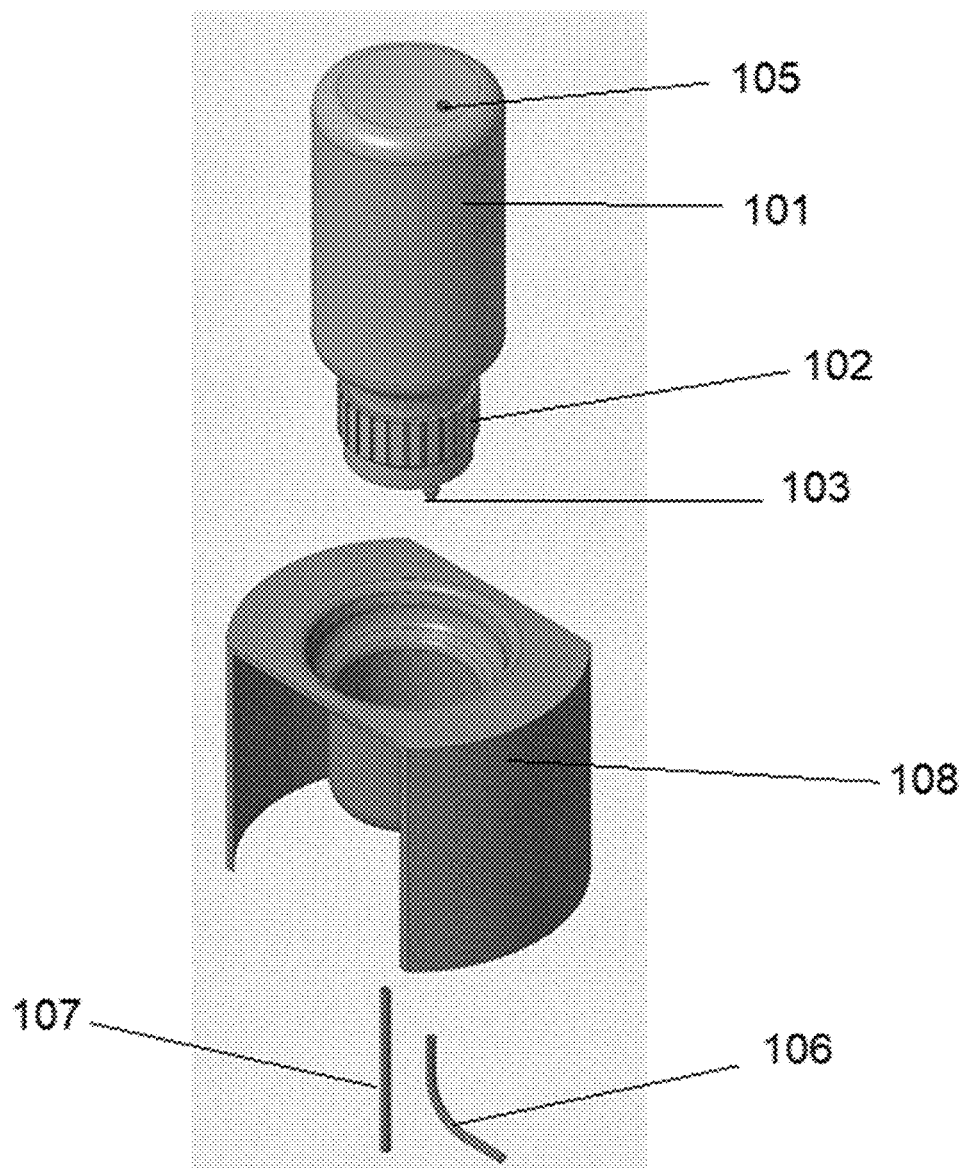

FIGS. 1A-E illustrate a salt canister 101 that can be used to generate brine for recharging zirconium phosphate in a reusable zirconium phosphate sorbent module. FIG. 1A is a perspective view of a salt canister 101; FIG. 1B is the salt canister 101 connected to fluid lines, FIG. 1C is a transparent view of an empty salt canister 101, FIG. 1D is a transparent view of a filled salt canister 101, and FIG. 1E is an exploded view showing the components used with the salt canister 101.

The salt canister 101, as illustrated in FIG. 1A can include an inlet 104, and outlet 103. The inlet 104 and outlet 103 extend through a cap 102 on the salt canister 101. FIG. 1B illustrates the salt canister 102 inserted into a base frame 108. In one non-limiting embodiment, the salt canister 101 can be generally cylindrical in form. However, one of ordinary skill will understand that any container of any suitable shape, size, or form capable of containing one or more materials of the invention can be used. For example, the salt canister 101 can be tapered or shaped symmetrically, or non-symmetrically to fit inside a compartment of another device, such as a recharger (not shown). The base frame 108 can be included to mount the salt canister 101. The base frame 108 holds the salt canister 101 in place during use and provides a space underneath the salt canister 101 for connection to fluid line 106 and fluid line 107 at the bottom of salt canister 101. Alternative methods of mounting the salt canister 101 can be used, including hooks or any other method known to one of skill in the art. An air vent 105 can be included in the salt canister 101 to allow air within the salt canister 101 to escape when water is added into the salt canister 101.

As illustrated in FIG. 1C, the inlet 104 and outlet 103 can extend through the cap 102 of salt canister 101. The outlet 103 can connect to a fluid line 106, which is fluidly connectable to a brine container (not shown). The inlet 104 can connect to a fluid line 107, which is fluidly connectable to both a water source and an acetic acid source (not shown). The base frame 108 can include holes to allow fluid line 106 and fluid line 107 to connect to inlet 104 and outlet 103, respectively. The inlet 104 can include a top portion 109 that extends upwardly into an interior of the salt canister 101. The top portion 109 of the inlet 104 can extend above a salt level inside the salt canister 101. A filter pad 112 can be included above the outlet 103. The filter pad 112 can block solid salt or any other material from exiting the salt canister 101, while allowing the generated brine solution to exit the salt canister 101. The filter pad 112 can be any type of filter that will prevent most solid salt particles from passing through while allowing the brine solution to pass through.

FIG. 1D illustrates the salt canister 101 filled with solid salts 110 as water 111 is added. In certain embodiments, the salt canister 101 can initially be about ¾ filled with the sodium acetate and sodium chloride, leaving about ¼ of the space available for filling with water. However, the actual amount of solid salts initially placed in salt canister 101 can vary. For example, the salt canister can initially be ½ filled, ⅔ filled, ¼ filled or any other fractional amount depending on the needs of the user. As illustrated in FIG. 1D, the inlet 104 can include a top portion 109 that extends upwardly into an interior of the salt canister 101 above a salt level of the solid salts 110. To generate a brine solution, water 111 can be pumped through the inlet 104. The water 111 can spray out of the top portion 109 of the inlet 104 to spread across a top of the salts 110. As the water 111 is added to salt canister 101, air can escape through vent 105. The water 111 can dissolve the sodium chloride and sodium acetate in the salt canister 101 and exit through outlet 103 in cap 102. Filter pad 112 can be included to prevent solid particles from entering outlet 103 or fluid line 107. The filter pad 112 can be placed between the solid salts 110 and the outlet 103 to filter brine solution exiting the salt canister 101. The base frame 108 can include holes to allow fluid line 106 and fluid line 107 to connect to inlet 104 and outlet 103, respectively.

FIG. 1E is an exploded view of the salt canister 101. The cap 102 of the salt canister 101 can be inserted into base frame 108. The base frame 108 can include openings for the inlet (not shown in FIG. 1E) and outlet 103 to connect to fluid lines 107 and 106, respectively. As water is pumped into the salt canister 101 through fluid line 107, air can escape the salt canister 101 through vent 105.

After the brine solution exits through the outlet 103 of salt canister 101 into fluid line 107, the generated brine solution can be collected in the brine container (not shown). The brine solution can be recirculated back to inlet 104 of the salt canister 101, through the outlet 103, and back through the brine container. The brine solution can be recirculated for a preset period of time, or until full dissolution of the solid salts 110 and after a homogeneous solution is formed in a recirculation flow path as further described in FIG. 2.

The salt canister 101 can be constructed from any material capable of holding the salts 110. In certain embodiments, the salt canister 101 can be constructed from a polymer such as polypropylene, polyethylene, or high-density polyethylene. Alternatively, metal, glass, or other materials can be used.

The required size of the salt canister 101 can depend on the amount of brine solution desired. As described, the salt canister 101 can initially be about ¾ filled with the sodium acetate and sodium chloride. The total volume of the salt canister can vary depending on the desired brine output volume. As a non-limiting example, the salt canister 101 can be sized about 2.5 L to hold between 1.5-2.0 kg of sodium acetate and sodium chloride with 200-300 mL left of water filling capacity. However, with larger brine outputs desired, the salt canister can be made larger as well. The volume of water added can be varied to generate a brine solution having a desired sodium concentration. In certain embodiments, about 5 L of water can be used to generate the brine solution. However, the amount of water used can be varied depending on the desired brine solution concentration and the amount of salt used.

Figure 2:
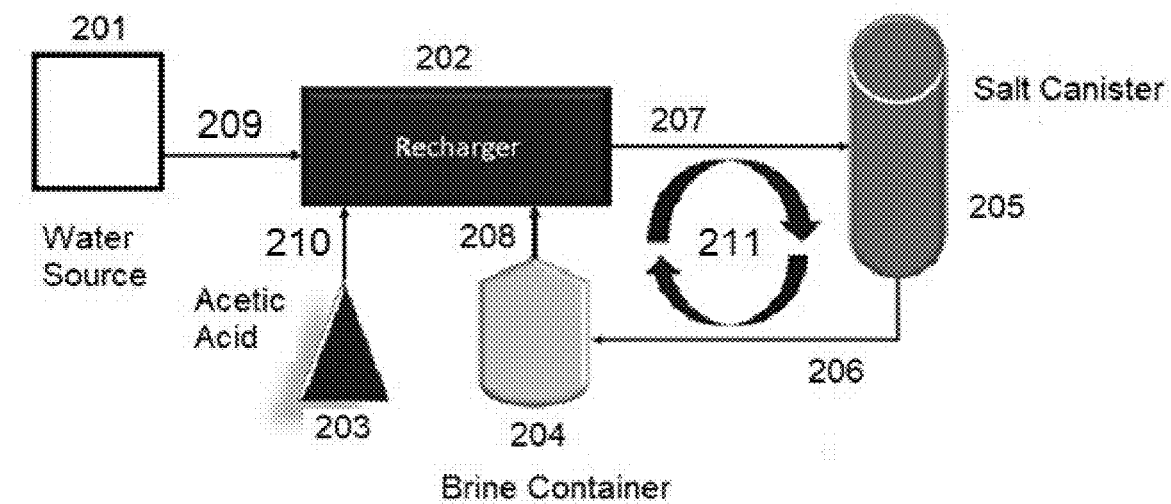
FIG. 2 illustrates a sorbent recharger system using a salt canister.

FIG. 2 is a generalized diagram of a sorbent recharger system using the described salt canister 205. As described, the salt canister 205 can contain sodium acetate and sodium chloride in any amount. Water from water source 201 can be pumped into an inlet of the salt canister 205. In certain embodiments, the water source 201 can be fluidly connected to a sorbent recharger 202. The water can be pumped from water source 201, through line 209 into the sorbent recharger 202, and then into the salt canister 205 through fluid line 207. Alternatively, a separate fluid line (not shown) can connect the water source 201 to the inlet of salt canister 205.

The water pumped into salt canister 205 can dissolve the sodium acetate and sodium chloride and exit through an outlet of the salt canister 205 into brine container 204. To ensure complete dissolution of the sodium acetate and sodium chloride and a homogeneous brine solution, the solution can be recirculated through a flow path as shown by arrows 211. The brine solution can be pumped from the outlet of the salt canister 205 into brine container 204 through fluid line 206, back into sorbent recharger 202 through fluid line 208, and then back to the inlet of the salt canister 205 through fluid line 207. The salt canister 205, fluid line 206, brine container 204, fluid line 208, recharger 202, and fluid line 207 define a recirculation flow path. The solution can be pumped through the recirculation flow path until a homogeneous solution is formed, or for some preset period of time that is long enough to ensure formation of a homogenous solution. The preset period of time can be any time long enough to ensure complete dissolution and homogeneity. In certain embodiments, the preset period of time can be between 20 and 45 minutes. Additionally, or alternatively, one or more sensors, such as conductivity sensors, can be included to ensure that the generated brine solution has the proper concentrations of sodium chloride and sodium acetate.

The brine solution, once formed, can be used to recharge zirconium phosphate in a zirconium phosphate sorbent module. The brine solution can replace cations that were bound to the zirconium phosphate during dialysis treatment with sodium and hydrogen ions. The final ratio of sodium to hydrogen ions on the recharged zirconium phosphate is a function of the pH and sodium concentration of the brine solution. As such, the sodium/hydrogen ratio of the recharged zirconium phosphate can be controlled by controlling the pH and sodium concentration of the brine solution used in recharging. Acetic acid from acetic acid source 203 can be added to the recirculation flow path while the brine is being recirculated to adjust the pH of the brine solution. Acetic acid can be pumped from acetic acid source 203 through fluid line 210 into the sorbent recharger 202 for addition to the recirculating flow path. A control system (not shown) can control one or more pumps and one or more valves within the sorbent recharger 202 to generate a brine solution having a specified pH by adding a volume of acetic acid from the acetic acid source 203. Using a known amount of sodium chloride and sodium acetate in salt canister 205 and adding a set amount of water from water source 201 can provide a known sodium concentration in the resulting brine solution. The amount of acetic acid added from acetic acid source 203 can be controlled by the control system to generate a brine solution having a desired pH.

To recharge the zirconium phosphate in a zirconium phosphate sorbent module, the control system can control one or more pumps (not shown) and/or valves (not shown) to pump the generated brine solution from brine container 204, through fluid line 208, into sorbent recharger 202 where the brine solution is passed through the zirconium phosphate sorbent module.

Table 1 shows a non-limiting example of a brine solution for recharging zirconium phosphate that can be made using the described salt canister system.

TABLE 1

| ZP Recharge-Brine Solution Preparation | | | | |
|---|---|---|---|---|
| Description | Sodium chloride | Sodium Acetate, trihydrate | Acetic Acid | Water |
| Conc M | 4.70 | 0.40 | 0.40 | N/A |
| Mol wt | 58.50 | 136.00 | 60.05 | N/A |
| Mix density (kg/l) @25° C. | | 1.19 | | |
| Individual density (kg/l) @25° C. | 2.16 | 1.45 | 1.05 | 1.00 |
| Total Volume (L) | | 6.20 | | |
| Total weight (kg) | | 7.38 | | |
| Individual weight (kg) | 1.70 | 0.34 | 0.15 | 5.19 |
| Individual volume (L) | N/A | N/A | 0.14 | 5.20 |

The brine solution described in Table 1 uses 5.20 L of water, which is added to a salt canister containing 1.70 kg of sodium chloride and 0.34 kg of sodium acetate trihydrate. 0.14 L of acetic acid can be added during generation of the brine solution, as described. The resulting brine solution has a sodium chloride concentration of 4.70 M, a sodium acetate concentration of 0.40 M, and an acetic acid concentration of 0.40 M. However, as described, brine solutions having a higher or lower pH can be generated by adding more or less acetic acid or sodium acetate. A person of ordinary skill in the art will understand that the ratio of sodium chloride to sodium acetate used can vary depending on the needs of the user. The sodium concentration of the brine solution can be controlled by using more or less sodium chloride and sodium acetate or by varying the volume of water added to the salt canister in forming the brine solution as would be understood by one of ordinary skill in the art. One or more conductivity sensors can be used to ensure complete dissolution and homogeneity. The conductivity of the generated brine solution will vary based on the concentrations of each solute. However, the conductivity of the solution shown in Table 1 should be within 180-240 mS/cm at 25° C.

Figure 3A:
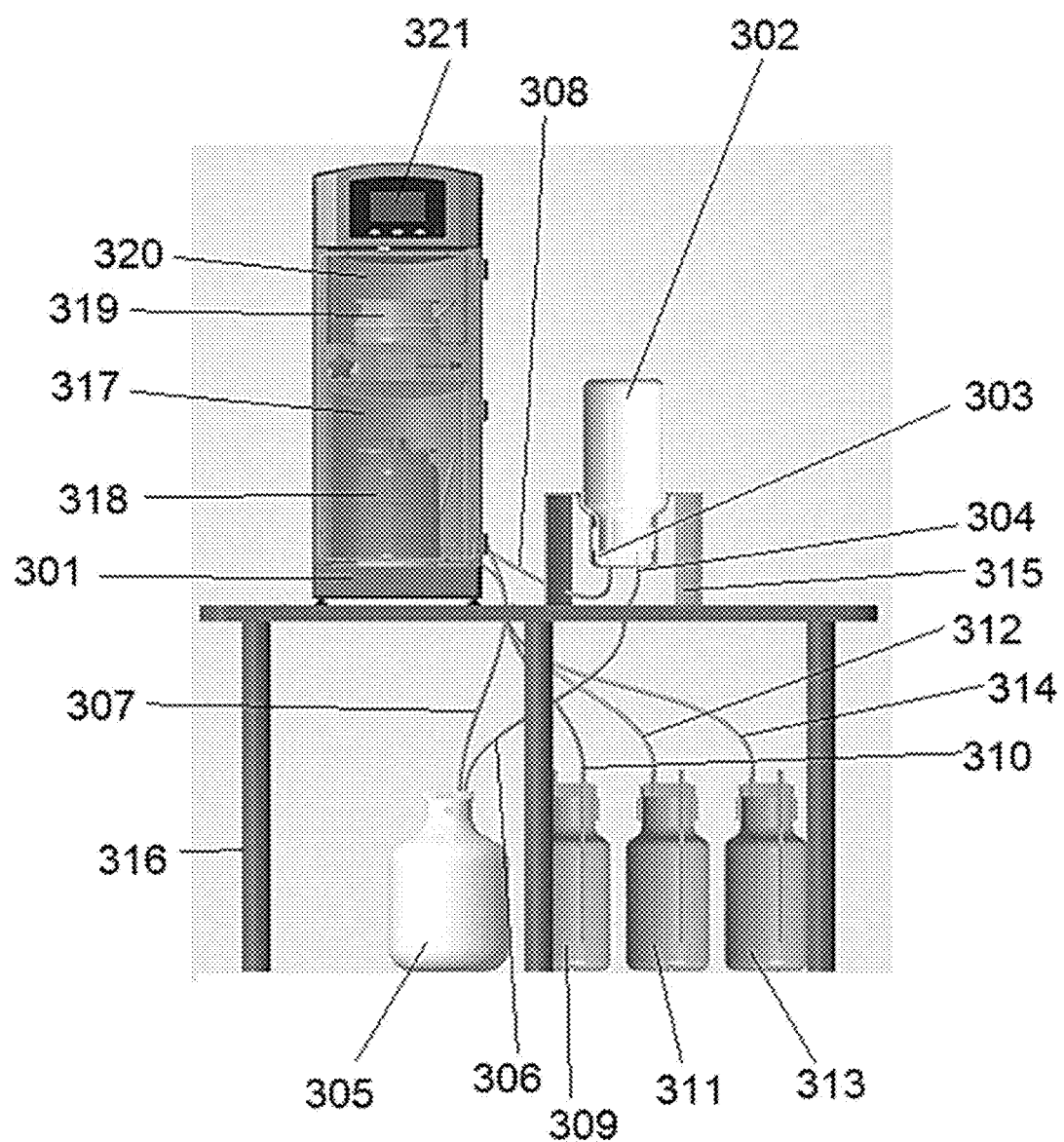
FIGS. 3A-B illustrate a sorbent recharger for recharging sorbent materials in reusable sorbent modules.
Figure 3B:
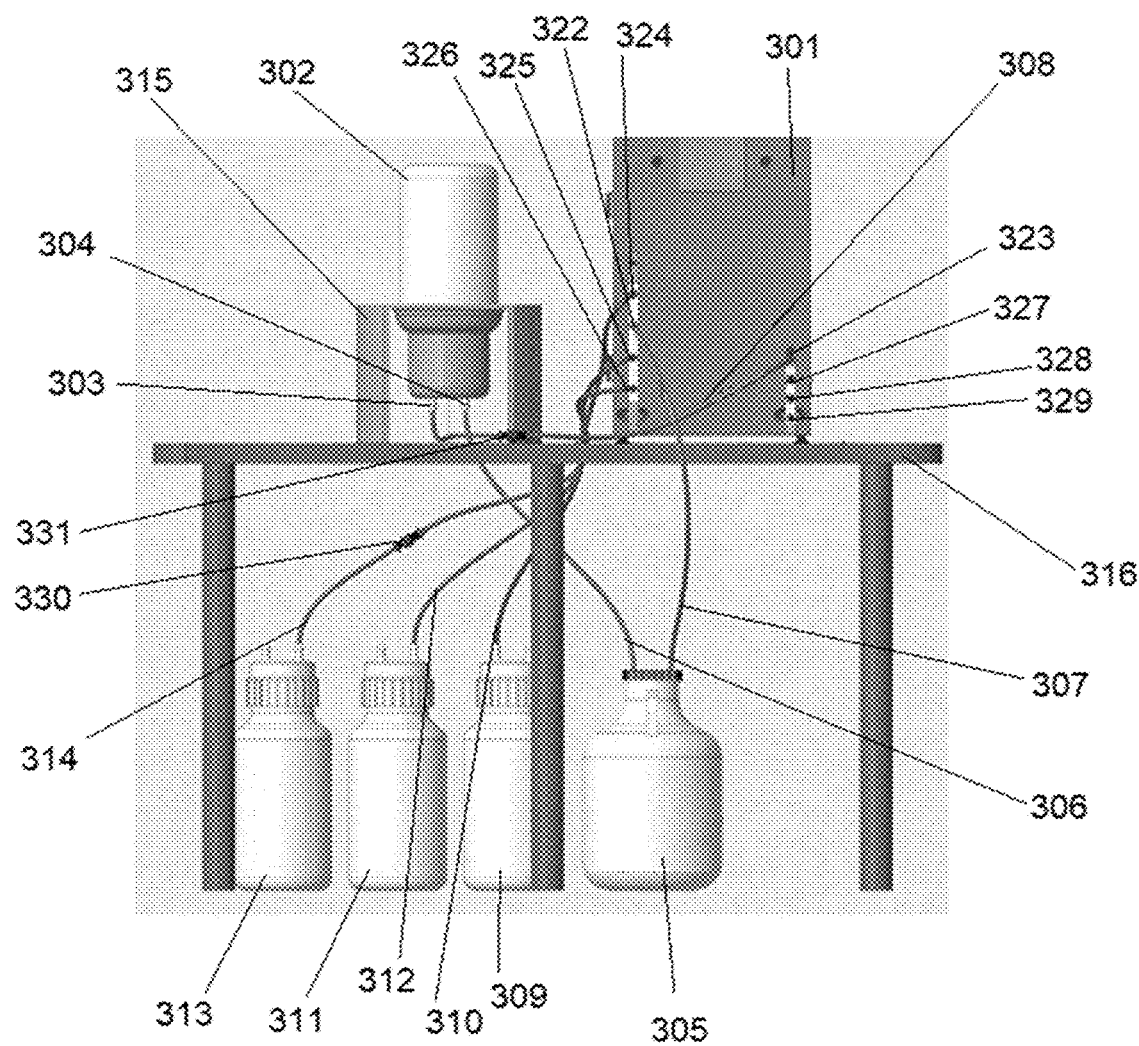

FIGS. 3A-B show a sorbent recharger 301 using a salt canister 302 as described. FIG. 3A is a front view of the sorbent recharger 301, while FIG. 3B is a rear view of the sorbent recharger 301. As illustrated in FIG. 3A, the salt canister 302 can be fluidly connected to the sorbent recharger 301. Water from a water source (not shown) can be pumped through an inlet 303 of the salt canister 302 containing sodium chloride and sodium acetate through fluid line 308. The brine solution formed can exit the salt canister 302 through outlet 304 and flow through fluid line 306 into brine container 305. The brine solution can be recirculated from the outlet 304 of the salt canister 302, through fluid line 306 and into the brine container 305, out of brine container 305 through fluid line 307 back to sorbent recharger 301, and then back into the salt canister 302 through fluid line 308. The brine solution can be recirculated in the flow path until a homogeneous solution is formed, or for a preset period of time. While the brine solution is recirculating, acetic acid from acetic acid source 309 can be pumped through fluid line 310 into sorbent recharger 301, where the acetic acid is added to the recirculating brine solution. After a homogeneous brine solution is formed, the brine solution can be collected in brine container 305. The salt canister 302 can be mounted in base frame 315 on table 316, or by any other means known in the art.

The sorbent recharger 301 can include one or more receiving compartments for receiving reusable sorbent modules. As illustrated in FIG. 3A, the sorbent recharger 301 includes a first receiving compartment 317 for receiving a zirconium phosphate sorbent module 318. To recharge the zirconium phosphate in the zirconium phosphate sorbent module 318, the generated brine solution in brine container 305 is pumped through the zirconium phosphate sorbent module 318, replacing potassium, calcium, magnesium, and ammonium ions bound to the zirconium phosphate with sodium and hydrogen ions.

In certain embodiments, additional receiving compartments can be included. For example, the sorbent recharger 301 shown in FIG. 3A includes a second receiving compartment 320 for receiving a zirconium oxide sorbent module 319. Additional chemicals can be included for recharging the zirconium oxide in zirconium oxide sorbent module 319. To recharge zirconium oxide, a basic solution can be pumped through the zirconium oxide sorbent module 319. Sodium hydroxide from sodium hydroxide source 311 can be pumped through fluid line 312 into sorbent recharger 301 and through the zirconium oxide sorbent module 319. Bleach from bleach source 313 can be pumped through fluid line 314 into sorbent recharger 301 and through the zirconium oxide sorbent module 319 to disinfect the zirconium oxide sorbent module 319. Alternatively, a sorbent recharger can include two receiving compartments to recharge two different zirconium phosphate sorbent modules. In any embodiment, the sorbent recharger 301 can include any number of receiving compartments for recharging any number of zirconium phosphate and/or zirconium oxide sorbent modules.

The sorbent recharger can include a graphical user interface 321 shown in FIG. 3A that can be used to control recharging of the sorbent materials. Through graphical user interface 321, the user can initiate, stop, and otherwise control the preparation of the brine solution and the recharging process. Further, any errors, alerts, or other messages can be provided to the user through graphical user interface 321.

As illustrated in FIG. 3B, the sorbent recharger 301 can include fluid inlet port 322 for receiving a brine solution from brine container 305, inlet port 324 for receiving acetic acid from acetic acid source 309, inlet port 325 for receiving sodium hydroxide from sodium hydroxide source 311, and inlet port 326 for receiving bleach from bleach source 313. An additional inlet port (not shown) can be included for receiving water from a water source (not shown). The sorbent recharger 301 can also include outlet port 323 for pumping fluid to the salt canister 302. Additional outlet ports, including outlet port 327, outlet port 328, and outlet port 329 can be included for connection to a drain, waste container, or collection container.

The salt canister 302 can connect to fluid lines 306 and 308 through any means known in the art. In FIG. 3B, the connections are shown as quick connector 331. A similar quick connector 330 can be used to connect bleach source 313 to fluid line 314. One of skill in the art will understand that connectors can also be used for connecting any of the fluid sources to the fluid lines. Quick connectors allow fluid lines to be connected by snapping connectors on each line together. However, other connectors that can form fluid passages can be used. As described, the salt canister 302 can be mounted on the system using base frame 315, or by any other method. In FIGS. 3A-B, the sorbent recharger 301 is sized to fit on a table 316. Larger sorbent rechargers can be used for recharging additional materials, as needed. An appropriate size of the sorbent recharger can be determined by one of ordinary skill in the art depending on the desired use case.

Figure 4:
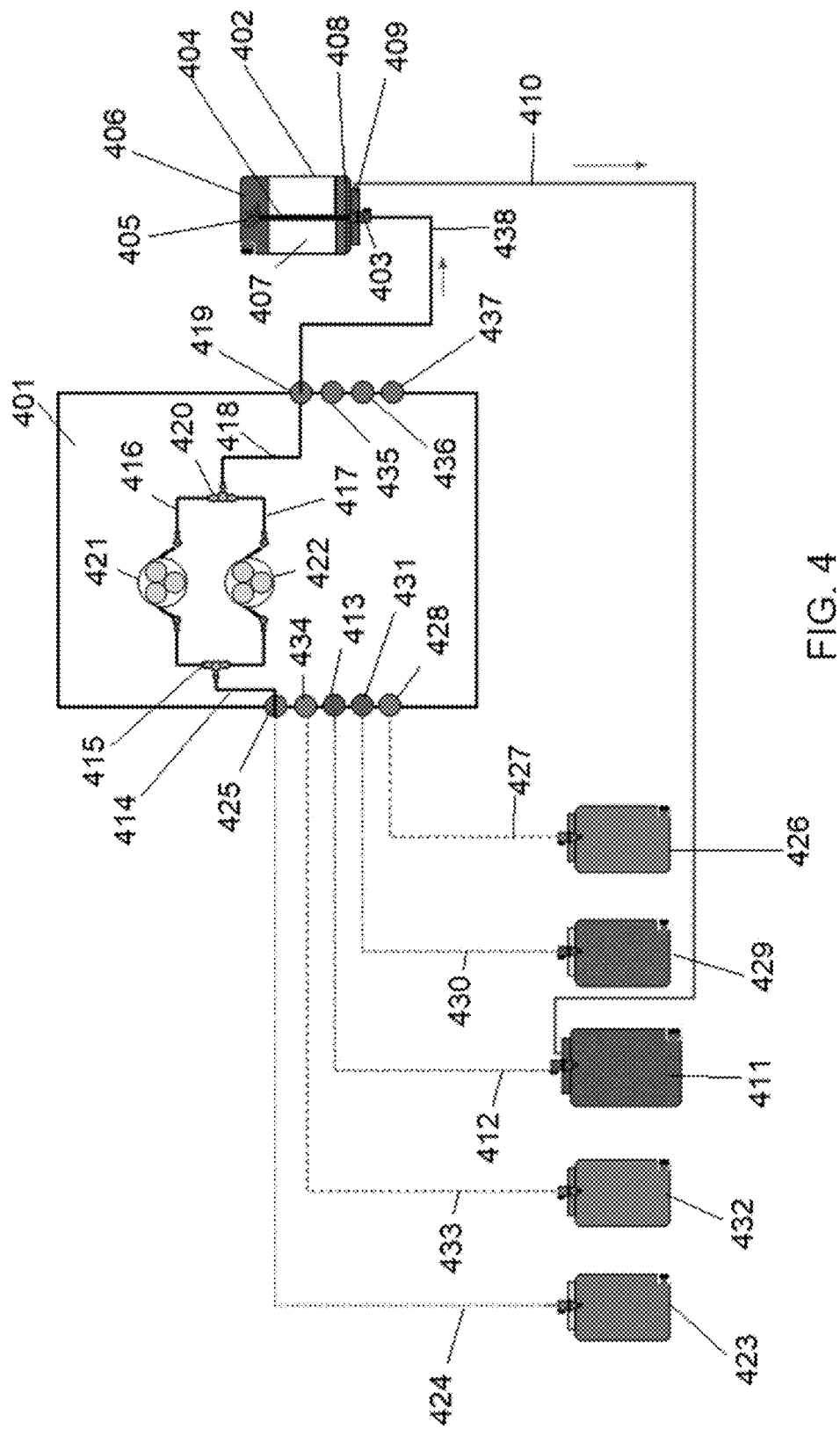
FIG. 4 shows a flow path for a sorbent recharger using a salt canister.

FIG. 4 shows a flow diagram for a recharger system using a salt canister. The salt canister 402 can include an inlet 403 with an upper part 404 extending upwardly into an interior of the salt canister 402. Solid sodium chloride and solid sodium acetate can be placed in a lower portion 407 of the interior of salt canister 402. Water from water source 423 can be pumped through water line 424 and port 425 into sorbent recharger 401. As illustrated in FIG. 4, in certain embodiments the sorbent recharger 401 can use two pumps 421 and 422. Using two pumps allows fluid from multiple sources to be mixed in-line rather than using mixing chambers. However, one of skill in the art will understand that a single pump system can also be used, or any number of suitable pumps with appropriate valve arrangements. From inlet port 425, the water is pumped through fluid line 414 and T-junction 415 into fluid lines 416 and 417. The water is pumped through T-junction 420 and fluid line 418 to port 419. From port 419, the water can flow through fluid line 438 and into an empty upper portion 406 of salt canister 402. The water 405 can spray out of the upper part 404 of the inlet 403 to soak the salt and generate the brine solution.

The water can dissolve at least a portion of the sodium acetate and sodium chloride in salt canister 402 and exit the salt canister 402 through outlet 409 into fluid line 410 and brine container 411. Filter pad 408 can be included between the sodium acetate and sodium chloride in the lower portion 407 of salt canister 402 to prevent solid material from entering fluid line 410. The brine solution can be recirculated through the flow path from brine container 411, through fluid line 412 and port 413 of the sorbent recharger 401 into fluid line 414, where the brine solution follows the same pathway as the water back into salt canister 402. During recirculation of the brine solution, acetic acid from acetic acid source 426 can be pumped through fluid line 427 and port 428 for addition to the brine solution recirculating in the flow path. Once the sodium acetate and sodium chloride are fully dissolved, the acetic acid is added, and a homogeneous brine solution is formed, the brine solution can be collected in brine container 411.

To recharge zirconium phosphate, a zirconium phosphate sorbent module can be placed in a receiving compartment (not shown) of the sorbent recharger 401. An inlet of the zirconium phosphate sorbent module can be connected to fluid line 414, and an outlet of the zirconium phosphate sorbent module can be fluidly connected to a drain or collection container (not shown). The control system can operate pump 421 and/or pump 422 to pump brine solution from brine container 411 through the zirconium phosphate sorbent module.

As described, in certain embodiments, the sorbent recharger 401 can include a receiving compartment for receiving a zirconium oxide sorbent module (not shown). To recharge zirconium oxide in a zirconium oxide sorbent module, bleach can be pumped from bleach container 429, through fluid line 430 to port 431. A separate flow path can direct the bleach solution through the zirconium oxide sorbent module to a drain or collection container. Sodium hydroxide from sodium hydroxide container 432 can be pumped through fluid line 433 and port 434, and then through the zirconium oxide sorbent module. Additional outlet ports can be included on the sorbent recharger 401, including outlet port 435, outlet port 436, and outlet port 437 for connection to waste collection containers, drains, or other components.

One of skill in the art will understand that FIG. 4 is a simplified diagram of a non-limiting embodiment of a sorbent recharger 401. Additional components, such as valves, sensors, additional pumps, and additional fluid lines can be included, as necessary. The control system can be programmed to control the pumps and valves to direct fluid through the proper flow paths for generating the brine solution and recharging the sorbent materials.

The described systems and methods allow for a "just in time" brine preparation. Rather than storing large quantities of premade brine solution, the salt canister system allows for preparation of the brine solution immediately before use. The time required to generate the brine solution using a salt canister can vary, but generally the generation of the brine solution will be under 1 hour, or about 45 minutes.

One skilled in the art will understand that various combinations and/or modifications and variations can be made in the described systems and methods depending upon the specific needs for operation. Various aspects disclosed herein may be combined in different combinations than the combinations specifically presented in the description and accompanying drawings. Moreover, features illustrated or described as being part of an aspect of the disclosure may be used in the aspect of the disclosure, either alone or in combination, or follow a preferred arrangement of one or more of the described elements. Depending on the example, certain acts or events of any of the processes or methods described herein may be performed in a different sequence, may be added, merged, or left out altogether (e.g., certain described acts or events may not be necessary to carry out the techniques). In addition, while certain aspects of this disclosure are described as performed by a single module or unit for purposes of clarity, the techniques of this disclosure may be performed by a combination of units or modules associated with, for example, a medical device.

What is claimed is:

1. A system, comprising:
   a sorbent recharger; the sorbent recharger comprising:
   i) a receiving compartment for a zirconium phosphate sorbent module;
   ii) at least a first fluid line fluidly connectable to an inlet of the zirconium phosphate sorbent module in the receiving compartment;
   iii) at least a second fluid line fluidly connectable to an outlet of the zirconium phosphate sorbent module;
   iv) at least one pump;
   a brine container fluidly connectable to the first fluid line;
   a salt canister; the salt canister comprising an inlet fluidly connectable to a water source and an acetic acid source; and an outlet fluidly connectable to the brine container; the salt canister containing sodium chloride and sodium acetate;
   a control system; the control system programmed to:
   i) pump a preset volume of fluid from the water source into the salt canister;
   ii) recirculate fluid in a first flow path from the outlet of the salt canister to the brine container and then to the inlet of the salt canister; and to
   iii) pump a preset volume of acetic acid into the first flow path.

2. The system of claim 1, the control system further programmed to pump fluid from the brine container through the zirconium phosphate sorbent module.

3. The system of claim 1, the control system programmed to recirculate fluid in a first flow path until a homogeneous solution is generated in the first flow path.

4. The system of claim 1, the control system programmed to recirculate fluid in a first flow path for a preset period of time.

5. The system of claim 1, wherein the salt canister comprises a filter pad between the sodium chloride and sodium acetate and the outlet.

6. The system of claim 1, wherein the salt canister comprises a cap on a bottom of the salt canister; wherein the inlet and outlet enter the salt canister through the cap.

7. The system of claim 6, wherein the salt canister comprises a filter pad in the cap; the filter pad between the sodium chloride and sodium acetate and the outlet.

8. The system of claim 1, wherein the inlet of the salt canister extends upwardly into the salt canister.

9. The system of claim 1, wherein the sodium chloride and sodium acetate are initially solid.

10. The system of claim 1, wherein the salt canister comprises an air vent at a top of the salt canister.

11. A method for generating a brine solution for recharging zirconium phosphate using the system of claim 1; comprising the steps of:
    pumping water from the water source to the salt canister through the inlet of the salt canister; the salt canister containing sodium chloride and sodium acetate;
    recirculating fluid from the outlet of the salt canister, to the brine container, and back to the inlet of the salt canister in the first flow path;
    pumping acetic acid into the first flow path; and
    collecting fluid from the first flow path into the brine container to generate the brine solution.

12. The method of claim 11; wherein the brine container is fluidly connected to the sorbent recharger; and further comprising the step of pumping the brine solution through the zirconium phosphate sorbent module in the sorbent recharger.

13. The method of claim 11, wherein the fluid is recirculated in the first flow path until a homogenous solution is generated.

14. The method of claim 11, wherein the fluid is recirculated in the first flow path for a preset period of time.

15. The method of claim 11, wherein the salt canister comprises a filter pad between the sodium chloride and sodium acetate and the outlet.

16. The method of claim 11, wherein the salt canister comprises a cap on a bottom of the salt canister; wherein the inlet and outlet enter the salt canister through the cap.

17. The method of claim 11, wherein the inlet of the salt canister extends upwardly into the salt canister.

18. A salt canister for use in recharging zirconium phosphate, the salt canister comprising:
    an inlet fluidly connectable to a water source;
    an outlet fluidly connectable to a brine container; and
    a cap on a bottom of the salt canister; wherein the inlet and outlet enter the salt canister through the cap;
    the salt canister containing sodium chloride and sodium acetate.

19. The salt canister of claim 18, further comprising an air vent on a top of the salt canister.

20. The salt canister of claim 18, wherein the inlet of the salt canister extends upwardly into the salt canister.

* * * * *